(12) United States Patent
Hill et al.

(10) Patent No.: US 11,298,483 B2
(45) Date of Patent: *Apr. 12, 2022

(54) DISPLAY AND CONTROLS FOR A CPAP DEVICE

(71) Applicant: ResMed Pty Ltd, Bella Vista (AU)

(72) Inventors: Phoebe Katherine Hill, Sydney (AU); Mark Bertinetti, Sydney (AU); Rohan Neil Primrose, Sydney (AU); Heike Thiele, Munich (DE); Alexander Virr, Gosford (AU); Andrew Mikael Price, Sydney (AU); Sandra Robyn Curtis, Blue Mountains (AU); Andrew Roderick Bath, Sydney (AU)

(73) Assignee: ResMed Pty Ltd, Bella Vista (AU)

(*) Notice: Subject to any disclaimer, the term of this patent is extended or adjusted under 35 U.S.C. 154(b) by 930 days.

This patent is subject to a terminal disclaimer.

(21) Appl. No.: 16/046,131

(22) Filed: Jul. 26, 2018

(65) Prior Publication Data

US 2018/0333550 A1    Nov. 22, 2018

Related U.S. Application Data

(63) Continuation of application No. 14/589,052, filed on Jan. 5, 2015, now Pat. No. 10,046,128, which is a
(Continued)

(30) Foreign Application Priority Data

Sep. 17, 2008  (AU) ................................ 2008904835
Oct. 1, 2008   (AU) ................................ 2008905107
May 28, 2009   (AU) ................................ 2009902445

(51) Int. Cl.
*A61M 16/00*   (2006.01)
*A61M 16/10*   (2006.01)
(Continued)

(52) U.S. Cl.
CPC .... *A61M 16/0066* (2013.01); *A61M 16/0051* (2013.01); *A61M 16/0069* (2014.02);
(Continued)

(58) Field of Classification Search
CPC .............. A61M 16/00; A61M 16/0051; A61M 16/0003; A61M 16/021; A61M 16/022;
(Continued)

(56) References Cited

U.S. PATENT DOCUMENTS 4,408,172 A   10/1983  Perdue
4,531,233 A    7/1985  Nelson
(Continued)

FOREIGN PATENT DOCUMENTS

DE   19 747 284   4/1999
EP    0 102 332   3/1989
(Continued)

OTHER PUBLICATIONS

Office Action dated Jan. 29, 2020 issued in European Application No. 09813892.8 (7 pages).
(Continued)

*Primary Examiner* — Michael J Tsai
(74) *Attorney, Agent, or Firm* — Nixon & Vanderhye P.C.

(57) ABSTRACT

A user interface for respiratory apparatus comprises a combination of a menu display (302), push buttons (304, 308, 310) and a rotary control dial (306). The user interface may include a menu control for detecting at least one parameter from the user's operation of the controls to navigate the menu and applying this to subsequent operation of the user interface controls. The user parameter may be a direction of operation of the rotary control dial which the user associates with a particular direction of navigation within the menu.

19 Claims, 10 Drawing Sheets

Related U.S. Application Data continuation of application No. 12/998,085, filed as application No. PCT/AU2009/001231 on Sep. 17, 2009, now Pat. No. 8,944,057.

(51) Int. Cl.
  *A61M 16/16* (2006.01)
  *A61M 16/06* (2006.01)

(52) U.S. Cl.
  CPC ........ *A61M 16/024* (2017.08); *A61M 16/109* (2014.02); *A61M 16/1095* (2014.02); *A61M 16/161* (2014.02); *A61M 16/0666* (2013.01); *A61M 16/107* (2014.02); *A61M 16/16* (2013.01); *A61M 2016/0027* (2013.01); *A61M 2016/0036* (2013.01); *A61M 2205/18* (2013.01); *A61M 2205/3368* (2013.01); *A61M 2205/505* (2013.01)

(58) Field of Classification Search
  CPC .......... A61M 16/024; A61M 2205/502; A61M 2205/505; A61M 2205/52
  See application file for complete search history.

(56) References Cited

U.S. PATENT DOCUMENTS

| | | | |
|---|---|---|---|
| 4,647,219 A | 3/1987 | Figler et al. | |
| 4,867,152 A | 9/1989 | Kou et al. | |
| 5,237,987 A | 8/1993 | Anderson et al. | |
| 5,270,689 A | 12/1993 | Hermann | |
| 5,398,676 A | 3/1995 | Press et al. | |
| 5,627,531 A | 5/1997 | Posso et al. | |
| 5,645,053 A * | 7/1997 | Remmers ............ | A61M 16/026 128/204.21 |
| 5,647,346 A | 7/1997 | Hölscher | |
| 5,881,723 A | 3/1999 | Wallace et al. | |
| 6,005,299 A | 12/1999 | Hengst | |
| 6,148,814 A * | 11/2000 | Clemmer ............ | A61M 16/024 128/200.24 |
| 6,188,407 B1 | 2/2001 | Smith et al. | |
| 6,279,574 B1 * | 8/2001 | Richardson ....... | A61M 16/0096 128/204.18 |
| 6,360,741 B2 | 3/2002 | Truschel | |
| 6,410,871 B1 | 6/2002 | Rarbach | |
| 6,543,449 B1 | 4/2003 | Woodring et al. | |
| 6,554,260 B1 | 4/2003 | Lipscombe et al. | |
| 6,591,834 B1 * | 7/2003 | Colla ................. | A61M 16/024 128/204.21 |
| 6,773,838 B2 | 8/2004 | Suzuki et al. | |
| 6,895,963 B1 | 5/2005 | Martin et al. | |
| 6,897,624 B2 | 5/2005 | Lys et al. | |
| 6,983,341 B1 | 1/2006 | Lim | |
| 7,100,608 B2 | 9/2006 | Brewer et al. | |
| 7,106,955 B2 | 9/2006 | Thudor et al. | |
| 7,314,046 B2 | 1/2008 | Schroeder et al. | |
| 7,942,380 B2 | 5/2011 | Bertinetti et al. | |
| 8,122,883 B2 | 2/2012 | Banner et al. | |
| 8,161,404 B2 | 4/2012 | Kolletzki | |
| 2002/0022973 A1 | 2/2002 | Sun et al. | |
| 2002/0056452 A1* | 5/2002 | Brewer ................. | A61M 16/00 128/202.22 |
| 2003/0062045 A1 | 4/2003 | Woodring et al. | |
| 2004/0118403 A1 | 6/2004 | O'Connor et al. | |
| 2004/0140189 A1 | 7/2004 | Ruegenberg | |
| 2005/0039305 A1 | 2/2005 | Chirumbolo | |
| 2005/0061321 A1* | 3/2005 | Jones ................. | A61M 16/0051 128/204.18 |
| 2006/0130836 A1 | 6/2006 | Wixey et al. | |
| 2006/0235877 A1* | 10/2006 | Richard ................ | A61M 16/06 |
| 2006/0278221 A1 | 12/2006 | Schermeier et al. | |
| 2007/0062533 A1 | 3/2007 | Choncholas et al. | |
| 2007/0169776 A1 | 7/2007 | Kepler et al. | |
| 2007/0175480 A1 | 8/2007 | Gradon et al. | |
| 2007/0193582 A1 | 8/2007 | Kwok et al. | |
| 2007/0215155 A1 | 9/2007 | Marx et al. | |
| 2007/0249331 A1 | 10/2007 | Sinivaara et al. | |
| 2008/0000477 A1 | 1/2008 | Huster et al. | |
| 2008/0041380 A1 | 2/2008 | Wallace et al. | |
| 2008/0072896 A1 | 3/2008 | Setzer et al. | |
| 2008/0072900 A1 | 3/2008 | Kenyon et al. | |
| 2008/0097175 A1 | 4/2008 | Boyce et al. | |
| 2008/0099017 A1 | 5/2008 | Bordewick et al. | |
| 2008/0167082 A1 | 7/2008 | Gurevich et al. | |
| 2008/0185009 A1 | 8/2008 | Choncholas et al. | |
| 2008/0202527 A1 | 8/2008 | Hutchinson et al. | |
| 2009/0069749 A1 | 3/2009 | Miller | |
| 2009/0113238 A1 | 4/2009 | Liu et al. | |
| 2009/0223514 A1 | 9/2009 | Smith | |
| 2010/0229867 A1 | 9/2010 | Bertinetti et al. | |
| 2011/0164002 A1 | 7/2011 | Hill et al. | |
| 2011/0308518 A1 | 12/2011 | Mcgroary | |
| 2012/0055476 A1 | 3/2012 | Choncholas | |
| 2015/0114390 A1 | 4/2015 | Hill et al. | |

FOREIGN PATENT DOCUMENTS

| | | |
|---|---|---|
| EP | 0 314 305 | 5/1989 |
| EP | 1127583 A2 | 8/2001 |
| EP | 2055337 A1 | 5/2009 |
| EP | 2 098 260 | 9/2009 |
| GB | 2 338 420 | 12/1999 |
| WO | 1997/006843 | 2/1997 |
| WO | 1998/011574 | 3/1998 |
| WO | 98/41267 | 9/1998 |
| WO | WO 01/32069 A2 | 5/2001 |
| WO | 2006/019323 | 2/2006 |
| WO | 2007/099093 A1 | 9/2007 |
| WO | WO 2007/099093 A1 | 9/2007 |
| WO | WO 2008/056993 | 5/2008 |
| WO | 2009/059359 | 5/2009 |
| WO | WO 2010/014020 | 2/2010 |
| WO | 2011/056080 | 10/2010 |

OTHER PUBLICATIONS

Non-Final Rejection dated Sep. 22, 2014 issued in related U.S. Appl. No. 12/734,469, filed Nov. 5, 2008, 36 pages.

Examination Report for corresponding New Zealand Application No. 591807, dated Aug. 16, 2012, 2 pages.

International Search Report for PCT/AU2009/001231, dated Jan. 28, 2010.

English Translation of the Notice on the First Office Action for corresponding CN Application No. 200980137016.4, dated May 28, 2013, 4 pages.

Extension of Time Granted mailed Jun. 25, 2015, together with Notice of Opposition to Grant of Patent (Section 21) and an Application Under Section 21(2) (Proviso) for an Extension of the Period for Giving Notice of Opposition filed Jun. 24, 2015 in New Zealand Application No. 615069 (4 pages).

Respironics RemStar Pro User Manual dated Feb. 28, 2006 referenced in Office Action dated Mar. 12, 2013 in U.S. Appl. No. 12/734,469 as NPL1.

Screen dump from http://directhomemedical.com/ds400-mseries-remstar-pro-cpap0machine.html referenced in Office Action dated Mar. 12, 2013 in U.S. Appl. No. 12/734,469 as NPL2.

New Zealand First Examination Report for Application No. 615069, dated Sep. 20, 2013 (2 pages).

New Zealand Further Examination Report corresponding to NZ Application No. 591807 dated Jun. 20, 2013, 2 pages.

New Zealand First Examination Report for Application No. 611919, dated Jun. 20, 2013, 2 pages.

Deadline for Counterstatement dated Aug. 28, 2015, First Amended Notice of Opposition to Grant of Patent (Section 21) and the Statement of Case filed Aug. 27, 2015 in New Zealand Application No. 615069 (22 pages).

Final Office Action dated Oct. 11, 2013 for U.S. Appl. No. 12/734,469 (37 pages).

(56) References Cited

OTHER PUBLICATIONS

Notice of the Second Office Action w/English Translation dated Feb. 8, 2014 for Chinese Application No. 200980137016.4 (14 pages).
Decision of Rejection w/English Translation dated Mar. 18, 2014 for Japanese Application No. 2011-626356 (4 pages).
Notice of Opposition dated Feb. 25, 2014 for New Zealand Application No. 611919 (2 pages).
Notice of Opposition to Grant of Patent (amended and clean copies) issued in corresponding New Zealand Application No. 611919, (4 pages), dated Jun. 23, 2014.
Statement of Case issued in corresponding New Zealand Application No. 611919 dated Jun. 23, 2014, (10 pages).
Decision of Commissioner issued in related New Zealand Application No. 615069 mailed Aug. 9, 2016 (14 pages).
Partial Supplementary Search Report issued in related European Application No. 09 81 3892.8, dated Nov. 16, 2017, 17 pages.
Supplemental Search Report issued in related European Application No. 09 813 892, dated Feb. 21, 2018, 14 pages.
Supplementary European Search Report issued in related European Application No. EP 09 81 3892, dated Feb. 21, 2018, 14 pages.

\* cited by examiner

Navigation Symbol Keys

806 - Push Start/Stop Button

810 - Push Setup Button

808 - Push Info Button

802 - Wait for a Period of Time

804 - Push Dial

814 - Turn Dial

824 - Push & Hold Dial for 3 seconds

FIG. 8

DISPLAY AND CONTROLS FOR A CPAP DEVICE

CROSS-REFERENCES TO RELATED APPLICATIONS

This application is a continuation of U.S. application Ser. No. 14/589,052, filed Jan. 5, 2015, now U.S. Pat. No. 10,046,128, which is a continuation of U.S. application Ser. No. 12/998,085, filed Mar. 16, 2011, now U.S. Pat. No. 8,944,057, which is the U.S. National Phase of International Application No. PCT/AU2009/001231 filed on Sep. 17, 2009 and claims priority to Australian Provisional Application No. 2008904835 filed Sep. 17, 2008, Australian Provisional Application No. 2008905107 filed Oct. 1, 2008 and Australian Provisional Application No. 2009902445, filed May 28, 2009. Each of the above identified applications is incorporated herein in its entirety.

FIELD OF THE INVENTION

The present technology relates primarily to a respiratory device with an improved user interface, and to user interfaces for the control of respiratory treatment devices and for other user-controlled devices.

BACKGROUND OF THE INVENTION

Continuous Positive Airway Pressure (CPAP) is the gold-standard treatment for people suffering from Sleep Disordered Breathing (SDB), such as Obstructive Sleep Apnea (OSA). Following diagnosis, patients typically buy or rent a CPAP device together with a suitable patient interface (such as a mask) that they must wear every night while sleeping, in order to receive therapy.

Patient compliance with therapy is a significant issue, and it is believed that amongst a number of factors including patient comfort, patients are more likely to comply with therapy when the device is easy to use. Hence an improved user interface can lead to improved health outcomes for patients.

SUMMARY OF THE INVENTION

An improved user interface in accordance with one aspect of the present technology comprises a combination of physical hardware in the form of switches, display and lighting together with various electronic components; the visual elements shown on the display and the process of navigating between, highlighting, selecting and adjusting relevant parameters of the device.

Another aspect of the present technology is that it is suitable for use with medical devices providing treatment for sleep disordered breathing.

Another aspect of the present technology is that it is suitable for controlling a device for providing a supply of air at positive pressure, for example a flow generator. Another aspect of the present technology is that it is suitable for controlling an optional humidifier. Another aspect of the present technology is that it is suitable for controlling an optional heated tube. Another aspect of the present technology is that it is suitable for controlling a delay timer/ramp in delivery of therapy, for example, a delay timer or ramp control of pressure.

Another aspect of the improved user interface of the present technology is that it is suitable to be used in a low light or darkened room. Another aspect of the present technology is that it is suitable for use by a person with dark-adjusted eyes. Another aspect of the technology is that it is suitable for people with reduced dexterity.

Another aspect of the invention relates to an improved user interface for a device, for example for a medical device such as a respiratory device for treatment of sleep disordered breathing, the device having a user-operable dial which controls selection of menu items from a display menu, wherein the device includes a menu control which determines a user preference from the user's operation of the dial and applies that preference to subsequent operation of the device.

In one form, the control interface comprises a control for a device, adapted to:
  cause entry to a display menu to occur at a known position in the menu;
  determine from operation of a control dial by the user in navigation of the menu at least one user parameter; and
  apply the determined user parameter to subsequent operation of the control dial within that menu.

The user parameter may also be applied to subsequent operation of the control dial by the user, for example within the same user session of the device.

In one form, the user parameter comprises a direction in which the user intuitively turns the dial to navigate the menu, for example the direction that the user initially turns the dial to navigate up or down the menu. This has been found by the applicant to vary from one person to another, with approximately an even split amongst a population sample.

Other aspects, features and advantages of the invention will become apparent from the following detailed description, when taken in conjunction with the accompanying drawings.

Further forms of the invention are also set out in the attached claims.

BRIEF DESCRIPTION OF THE DRAWINGS

Further preferred embodiments of the invention will now be described with reference to the accompanying drawings, in which:

FIG. 8 shows a list of symbols representing operation of controls for a sample user interface further illustrated in FIGS. 9 and 10.

DETAILED DESCRIPTION OF PREFERRED EMBODIMENTS

1. Respiratory Treatment Device

The present invention will be described with respect to a flow generator (FG) for providing air or other breathable gas to a patient, for example a servo controlled blower for CPAP treatment of sleep disordered breathing (SDB).

Figure 1:
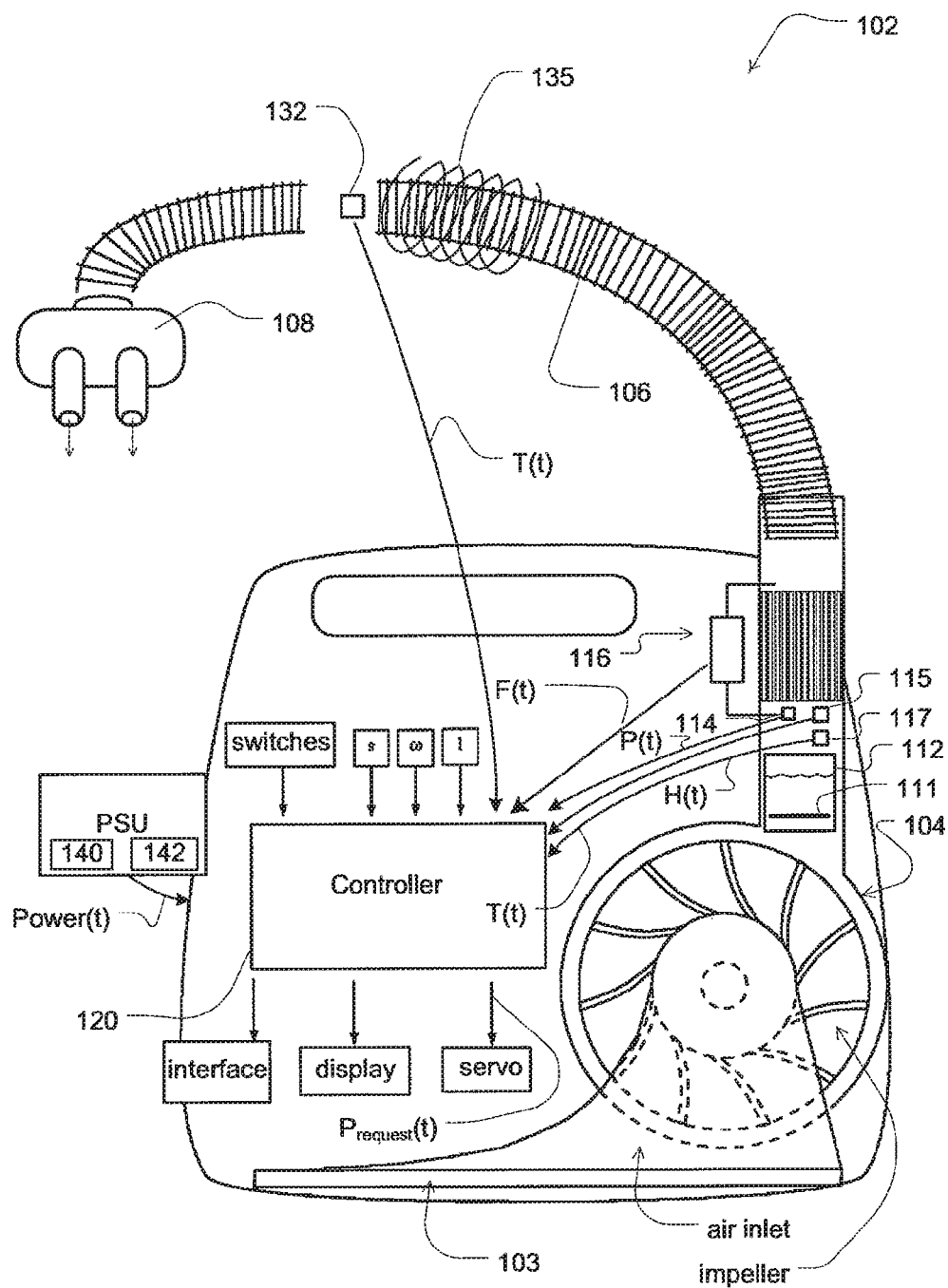
FIG. 1 shows example components of an apparatus for respiratory treatment of the upper airway of a patient.
Figure 2:
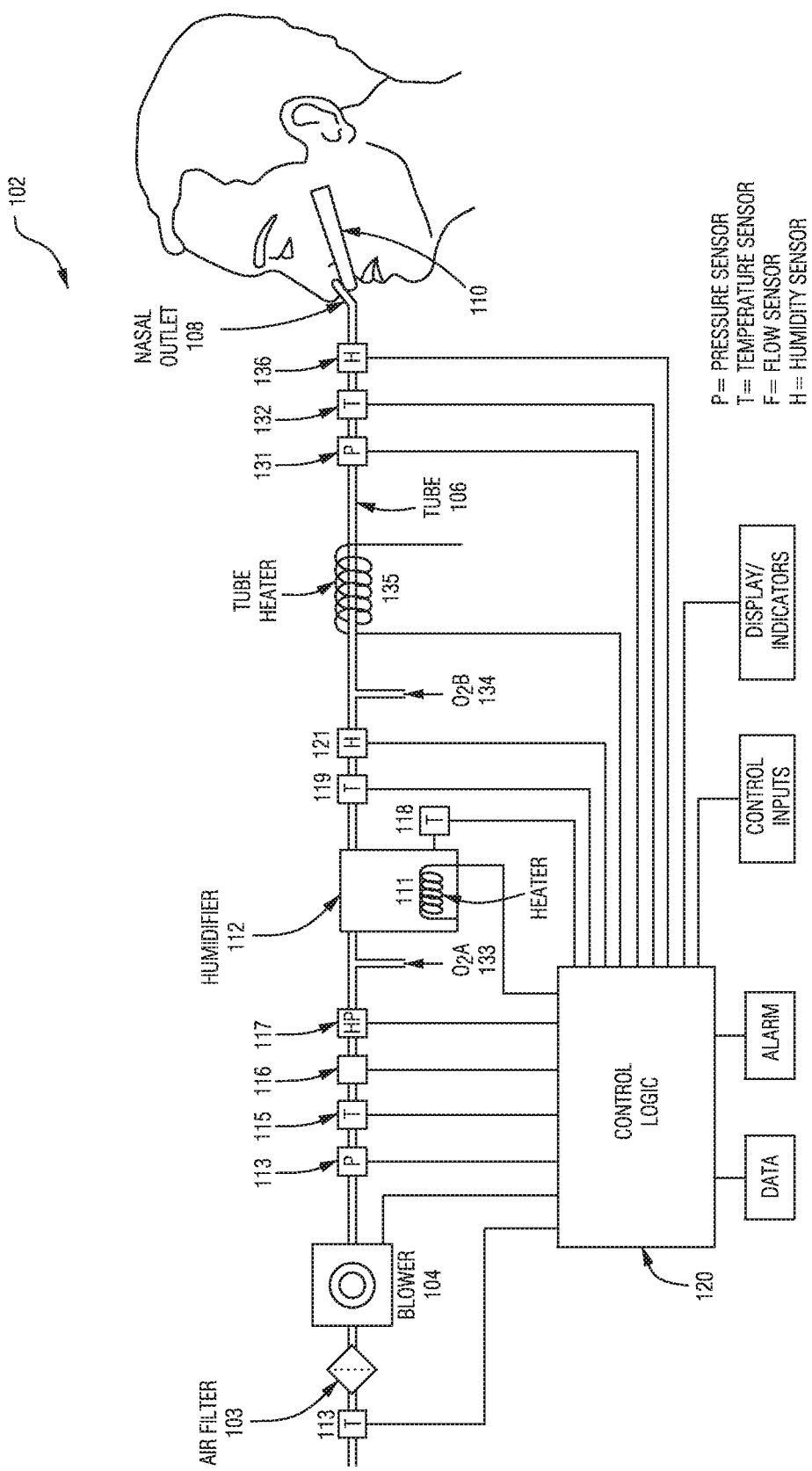
FIG. 2 illustrates an embodiment of a control relationship of components of the apparatus for respiratory treatment of FIG. 1.

The flow generator may be part of a respiratory treatment device 102 that may include some or all of the components illustrated in FIGS. 1 and 2. For example, the respiratory treatment device will typically include a flow generator such as a servo-controlled blower 104. The blower 104 will typically include an air inlet and impeller driven by a motor (not shown). Optionally, the air inlet may be coupled with a gas supply, such as for oxygen, to mix with or supplement the breathable gas supplied by the impeller to the airway of a user. Moreover, an air filter 103 may be provided, such as a FIEPA filter, to remove dust or other allergens from the air drawn into the air inlet. The blower may optionally be configured for generating varied flows or varied pressures associated with a patient respiratory cycle depending on the type of treatment (e.g., continuous level, bi-level, varying level etc. such as a pressure in an example range of 4 to 15 cmH2O or 4 to 25 cmH2O) and it may further be adjusted based on respiratory conditions (e.g., apnea, hypopnea, obstruction, etc.) detected by the apparatus (e.g., apnea, hypopnea, obstruction, etc.).

The respiratory treatment device 102 will also typically include a patient interface such as a flow delivery conduit 106 and nasal prongs or nasal cannula 108 to carry the flow of air or breathable gas to the upper airway of a user of the device or patient. The blower 104 can be coupled with the air delivery conduit 106 and the nasal cannula 108 so as to provide the breathable gas from the blower 104. Optionally, the patient interface may include a mask (not shown) coupled with the delivery conduit.

Operation of the respiratory treatment delivery apparatus may be controlled by one or more controller or processors 120, which may be for example a digital microprocessor.

The controller 120 receives signals supplied from various sensors, such as those described in more detail below, and applies a control logic to control the functions of the device, for example to control the operation of the blower 104 and of the humidifier heater 111.

The controller or processor 120 is typically configured and adapted to implement particular control. Thus, the controller may include integrated chips, a memory and/or processor control instructions or data in an information storage medium. For example, programmed instructions encompassing such a control methodology may be coded on integrated chips in the circuits or memory of the device or such instructions may be loaded as software or firmware using an appropriate medium.

The sensors may include one or more pressure sensors 114, 131 such as a pressure transducer. The pressure sensor 114 can be configured to measure the pressure generated by the blower 104 and/or supplied at the nasal cannula or patient airway. In the illustrated embodiment, the pressure sensor 114 is proximate to the blower 104. An additional or alternative pressure sensor 131 may be located downstream of the blower such as in the patient interface. The pressure sensor generates a pressure signal p(t) indicative of the measurements of pressure at its particular location.

In some embodiments, the respiratory treatment delivery device may optionally include one or more flow sensors 116. For example, flow through the nasal cannula 112 may be measured using a pneumotachograph and differential pressure transducer or similar device such as one employing a bundle of tubes or ducts to derive a flow signal F(t). Although the flow sensor is illustrated in FIG. 1 in a location proximate to the blower, the flow sensor may optionally be located closer to the patient, such as in the patient interface or nasal cannula 108.

Optionally, the patient interface and/or blower may also include accessory devices for patient comfort such as a humidifier 112 and humidifier heater 111. The humidifier device may be configured or controlled to heat and/or humidify the breathable gas to a desired temperature and/or humidity. For example, the device may include a reservoir or fluid circuit for passing the breathable gas through or proximate with a fluid or vapour of the reservoir or fluid circuit. The heater 111 may include one or more heating elements and/or heating plates to heat the fluid to create the vapour Additional accessory devices may also be implemented with the respiratory treatment device. For example, a heater or heating element(s) such as a delivery tube heater 135 may optionally be provided in or on the delivery tube of the patient interface to assist in maintaining the temperature of the breathable gas after it passes from the humidifier or flow generator.

For purposes of regulating the temperature and/or humidity of the breathable gas with the heating elements, the apparatus may also include one or more humidity sensors 117, 121, 136 and/or one or more temperature sensors 115, 118, 119, 132. The sensors generate temperature or humidity signals (illustrated as T(t) and H(t) ire FIG. 1) for controlling or setting temperature and/or humidity of the comfort devices. Optionally, some of the sensors may be located for measuring ambient conditions. Thus, these sensors would be located away from the heaters and humidifier chamber so as to provide a more accurate reading of ambient conditions.

The controller or processor 120 also communicates with a user interface of the device which includes control inputs such as buttons, dials for user control of the device, and a display such as a screen and/or indicator lights for indicating the device status and displaying control menus and the like to help the user select and control operations of the device. In some embodiments, some or all of the functions of the display and the user controls may be combined, for example by incorporating a touch screen display.

2. Modes of Operation

The embodiments of the invention will be further described with reference to preferred modes of operation as defined below:

Standby mode: When the FG is not delivering pressure.

Mask Fitting mode: When the FG provides a set pressure that allows the user to check for leaks between the mask & face, and to adjust the fit of the mask to minimise them.

Run mode: Then FG is delivering pressure for the purpose of therapy (includes pressure ramping).

Error mode: When the FG has detected an error and is currently not delivering therapy.

3. User Interface States of Operation

The following user interface (UI) states of operation are referred to:

No Power state: When the system has no mains power connected either no power cord, a power cord with wall socket switched off, or a loss of mains power.

Power Save state: When the Start/Stop key has been pushed and held for over 3 seconds, and the UI has been switched off except for the dim green LED backlight of the Start/Stop Button.

Setup state: When a user is interacting with the UI controls and the FG is in Standby Mode. Note: This is always the first state that the comes to when the Power is connected.

Adjust state: When a user is interacting with the UI controls and the FG is in Run Mode Warming Up state: When a user has activated the Warm Up function to pre-heat the humidifier (and heated tube) to the set value. The Warming Up state shall preferably be able to be stopped by selecting the Warming Up bar with the push button dial and pressing the dial to stop the Warming Up.

The Warming Up Function shall preferably only be available when the Humidifier or Climate Control setting is greater than zero, however the warming up state will warm up both the humidifier and the heated tube to their set levels.

Warming Ready state: When the humidifier and heated tube have reached their settings and the system is ready for use. The system stays in this state until a 30 minute time out is reached (taken from the start of Warming Up). The Warming Ready state shall be able to be stopped by selecting the Warming Ready bar with the push button dial and pressing the dial to stop the Warming Ready state.

Cool Down state: When the humidifier and heated tube have been in use during the Warming Up state, Warming Ready state, or Run mode, and the mode is changed to Standby Mode (eg pushing the Start/Stop button dining Run mode, or stopping the Warm Up function). This state is maintained for a duration that allows the Humidifier to cool down. The purpose of this state is to minimise condensation build up in the system.

Idle state: When the user has not touched the controls for 2 minutes during Standby mode, the UI shall "rest" with only the Start/Stop button illuminated and the LCD backlight faded to dim so that it is still readable.

Preferably this does not apply to the Warming Ready or Cool Down states.

Sleep state: When the user has not touched the controls for 2 minutes during Run mode, the UI shall go to "sleep" with only the Start/Stop button illuminated.

Preferably this does not apply to the Mask Fit or Error states.

Mask Fit Standby state: Used when Mask Fit mode is activated from the Standby mode by pushing and holding the dial. If the user does not push anything, this state will time out after 3 minutes and will automatically bring the device to the Run Mode in the Adjust State.

Mask Fit Run state: Used when Mask Fit mode is activated from the Run mode by pushing and holding the dial. This is predominantly for patients, who wish to perform a Mask Fit, but have inadvertently activated Run mode via SmartStart when putting on their mask.

If the user does not push anything, this state will time out after 3 minutes and will automatically bring the device hack to Run Mode in the Adjust State.

Alert state: Therapy continues and the UI displays an alert message over the Menu Page on the LCD and flashes a bright blue LED to indicate the alert state. Note: If the user alert has been disabled, the message will still appear but the LED will not flash. The alert message and LED can be cleared by fixing the issue that caused the alert or they can be temporarily cleared when any key is pressed and normal navigation is resumed. If the issue that caused the alert is not fixed then the alert message will re-appear after a time out period.

Two further states are specified—a patient menu state and a clinical menu state. In the clinical menu state, additional parameters are displayed and controllable when compared to the patient menu state. In addition, the parameters that are displayed and controllable in the patient menu are determined from the Clinical menu. For example, a clinician may decide that certain menus are available to one patient, and a different set of menus should be available for a different patient. In addition, the clinician can decide what information shall be displayed for the patient during or after treatment. For example, the clinician may decide whether to display such information as a "Sleep Quality Indicator" to the patient, and whether to display an Apnea Hypopnea Index (AHI).

While various preferred time intervals are specified, in other forms, other time intervals may be used.

4. User Interface Hardware

In one embodiment a user interface according the present technology, comprises:

a start/stop button a display (preferably a colour display)

two menu keys (preferably an information key and a setup key); & a push-button dial.

Figure 3:
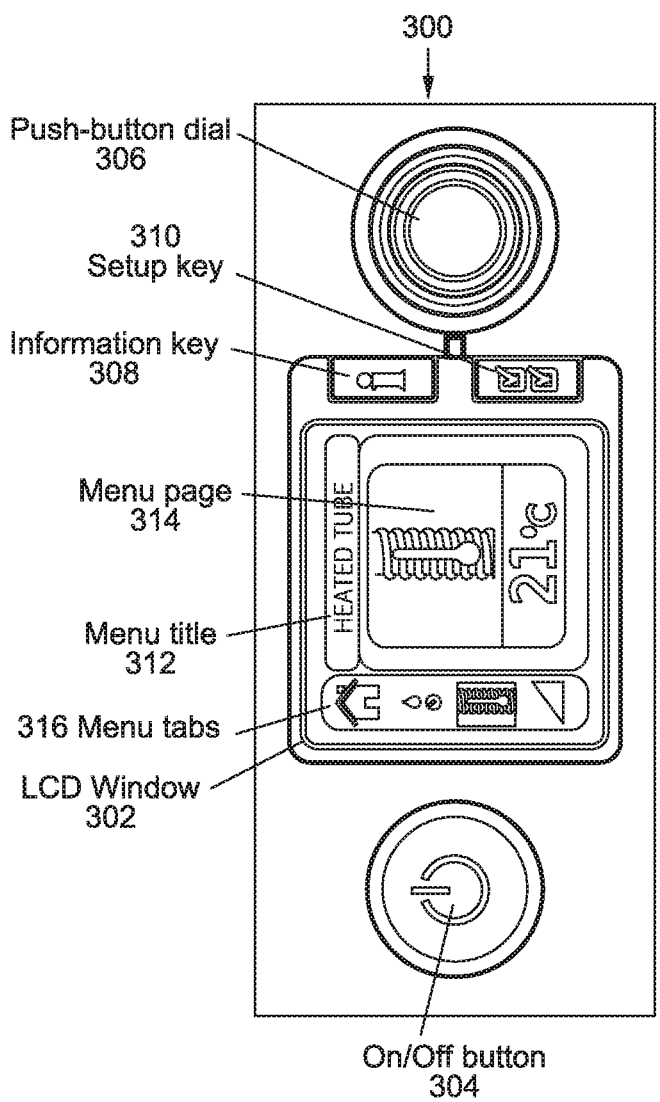
FIG. 3 shows a preferred layout of controls in accordance with the present technology.

An example of a user interface 300 is shown in FIG. 3, which includes a display 302, such as an LCD window or other suitable display for display of text and/or graphical information to the user, a start/stop (or on/off) button 304 at one side of the display for press control by the user, and a push-button dial 306 which incorporates both rotary dial and push button controls. In addition, there are push button controls 308, 310 at the side edge of the display, for example an information (or "info") key 308 denoted by the standard "i" symbol and a setup key 310 denoted by two tick symbols.

The illustrated display includes at its top a menu title 312, below that has a menu page 314 for displaying menu information to the user, and has a series of menu tabs 316 along one side of the menu page for tabbing through different menu pages.

In one form, the user interface further comprises a humidifier indicator light.

Figure 4:
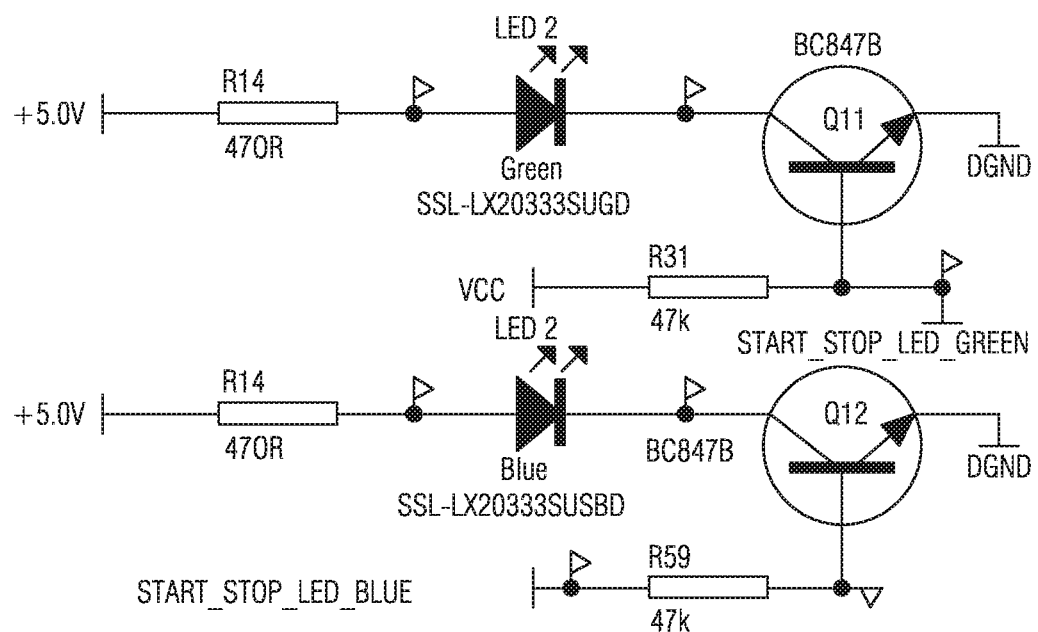
FIG. 4 shows a schematic of the components relating to the start/stop buttons.

Schematic diagrams of electrical circuits suitable for implementing embodiments of the present technology are shown in FIG. 4 to FIG. 7:

FIG. 4 shows a schematic of the components relating to the start/stop buttons.

Figure 5:
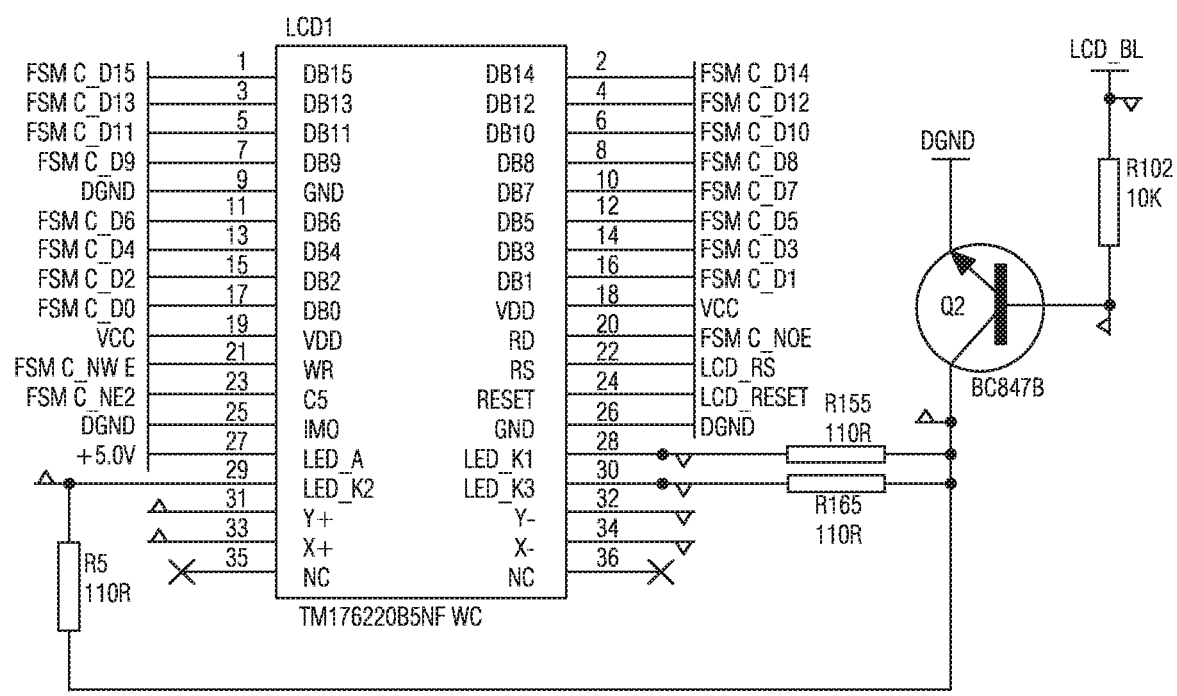
FIG. 5 shows a schematic of the components relating to the LCD display.

FIG. 5 shows a schematic of the components relating to the LCD display.

Figure 6:
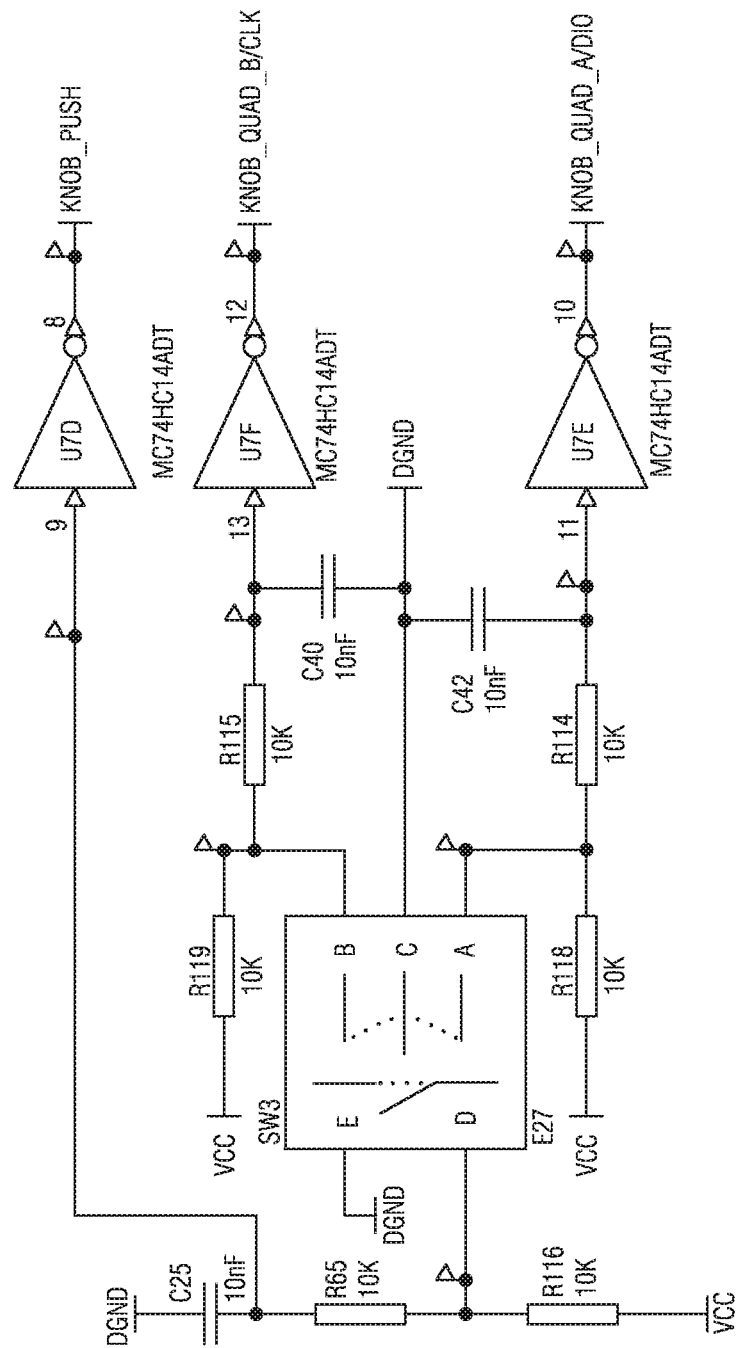
FIG. 6 shows a schematic of the components relating to the push-button dial.

FIG. 6 shows a schematic of the components relating to the push-button dial.

Figure 7:
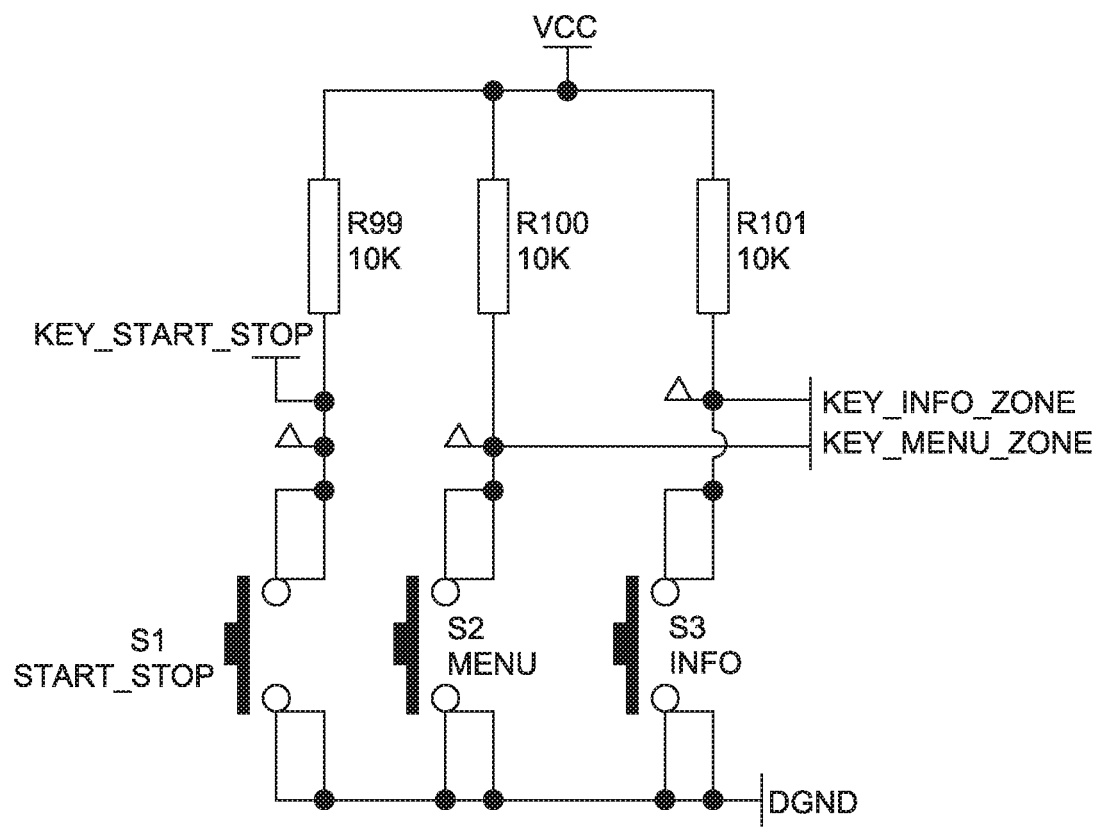
FIG. 7 shows a schematic of the components relating to the menu keys.

FIG. 7 shows a schematic of the components relating to the menu keys.

5 Navigation

In one embodiment, a control scheme for the present device comprises three main screens:

A home screen;

An information screen; &

A setup screen.

Each main screen displays at least one parameter. Where there is more than one parameter, turning the dial leads to each included parameter being highlighted in turn. Whilst a parameter is highlighted, it may be selected by pressing the dial. Parameter adjustments may be made by rotating the dial. Parameter adjustments may be confirmed by pressing the dial.

Preferably the home screen is the default screen that is displayed when the device is in standby mode or run mode. Pressing the start/stop button 306 will adjust the device between the standby mode and the run mode.

Pressing once on the first push button control 308 results in the information screen being displayed. Pressing a second time on the first push button control 308 results in a return to the home screen.

Pressing once on the second push button control 310 results in the setup screen being displayed. Pressing a second time on the second push button control 310 results in a return to the home screen.

In one form, the home screen displays information about a current patient treatment session when the device is in nm mode.

From the home screen, selecting the information menu key 308 once results in display of parameters defining the current treatment session, for example, the CPAP pressure. Selecting the information key once again, results in a return to the home screen.

From the home screen, selecting the settings menu key 310 once results in display of parameters that may be adjustable, for example the mask setting. Selecting the settings key 310 once again results in a return to the home screen.

The control scheme of the present device facilitates rapid navigation and display of patient treatment information, as well as facilitating adjustment of parameters where appropriate.

Preferably the display is 220 pixels×176 pixels, or larger. Preferably the display can show colours.

When starting Run Mode in the Patient Menu the display will change from the current display to a default screen. If the Humidifier is connected, or Climate Control is enabled, then the screen will default to the Humidifier or Climate Control setting so that if the patient needs to adjust the humidification during the night, they do not have to navigate anywhere, and they can simply reach over, turn the dial (which has highly tactile indents) and easily adjust their humidification level without looking.

6 Backlighting

In a preferred form the start/stop button 306, the display 302 and the humidifier indicator include backlighting. In a preferred form, certain colours are used: Green, Blue and Orange are used. However other colours may be used. When a light changes state, the transition may be gradual, for example, over 3 seconds. In other forms, the transition may be more rapid, or slower, or instantaneous.

6.1 Start/Stop Button backlighting:

In one embodiment, operation of the backlighting of the start/stop button 306 is used to provide the user with information on the device status, as described below.

Preferably when the device enters Power Save State the Start/Stop backlight fades over 3 seconds to DIM GREEN.

Preferably when the device is "Ready for use", ie when it enters the Setup State, the Start/Stop backlight fades over 3 seconds to BRIGHT GREEN.

Preferably when in the Standby Mode, and the UI is left for the Idle period, the Start/Stop backlight remains BRIGHT GREEN.

Preferably when the device enters Warning Up, or Warming Ready States, the Start/Stop backlight remains BRIGHT GREEN.

Preferably when the device enters the Cool Down State, from run mode the Start/Stop backlight fades over 3 seconds to BRIGHT GREEN.

Preferably when going to Run Mode and delivering therapy, or entering the Mask Fit Run State, the Start/Stop backlight becomes DIM BLUE within 0.5 seconds of entering this mode. The BLUE LED remains DIM whilst in use unless there is an error, and then it shall be BRIGHT BLUE FLASHING.

By providing the DIM BLUE light for run mode, and turning BRIGHT BLUE FLASHING only in event of error, the comfort, of the patient and any bed partner is enhanced by not having a bright LED in the bedroom when trying to sleep. The time periods and transitions described above are by way of example, and may be varied.

6.2 Display Backlighting:

Preferably when the device enters Power Save State the LCD backlighting fades over 3 seconds from ON to OFF.

Preferably when the device enters the Setup State, Adjust State, Mask. Fitting State, or it is awakened from the Idle or Sleep states by pressing any keys or pressing/turning the Push Button Dial, the LCD backlighting fades over 3 seconds from OFF to ON.

Preferably when the device enters the Warming Up, Warming Ready or Error State, the LCD backlight becomes ON within 0.5 seconds of entering these States.

Preferably when the device enters the Cool Down State, from run mode the LCD backlight fades over 3 seconds to ON.

Preferably when in Standby mode and the UI is not interacted with for the Idle period, the LCD backlight fades over 3 seconds to DIM.

Preferably when in Run mode and the UI is not interacted with for the Sleep period, the LCD backlight fades over 3 seconds to OFF.

Fading of the device between the ON, DIM or OFF positions allows the patient's eyes to adjust to the change in brightness in the middle of the night when the device state is changed, for example if the patient wakes up the device or stops it to go to the toilet. Fading to DIM during Standby mode will help save power, yet still provide some backlight for the patient to read the LCD display. Fading to OFF in the Run mode both saves power and minimises brightness in the bedroom, as during the Run mode the patient will have no need to read the LCD display.

6.3 Humidifier Backlight:

Preferably when the device enters the Power Save State the Humidifier Indicator backlight fades over 3 seconds to OFF.

Preferably when the device enters the Setup State the Humidifier Indicator backlight fades over 3 seconds to BRIGHT BLUE.

Preferably when the device enters the Mask Fit Standby State, the Humidifier Indicator backlight remains the same as the state from which Mask Fit was activated from, and returns back to that state when Mask Fit is complete.

Preferably the Humidifier Indicator backlight becomes BRIGHT BLUE within 0.5 seconds of entering the Error State with the Humidifier set to zero.

Preferably the Humidifier Indicator backlight becomes BRIGHT ORANGE within 0.5 seconds of entering the Warming Ready, Cool Down or Error State with the Humidifier set between 0.5 and 6.

Preferably when the device enters the Warming Up State, the Humidifier Indicator backlight fades over 3 seconds to DIM ORANGE.

Preferably when in the Standby or Run Mode, and the UI is left for the Idle or Sleep period, the Humidifier Indicator backlight is turned OFF.

Preferably when entering the Adjust State or Mask Fit Run State, the Humidifier Indicator backlight fades over 3 seconds to either: a DIM ORANGE if either the Humidifier or Heated Tube are set between 0.5 and 6; or a DIM BLUE if both the Humidifier and Heated Tube are set to zero.

The above-described display and BRIGHT, DIM and OFF backlighting states, and the fading between them, are used for similar reasoning as described previously in relation to the Start/Stop button and Display backlighting.

7 Intuitive Control Dial Arrangement

Figure 9:
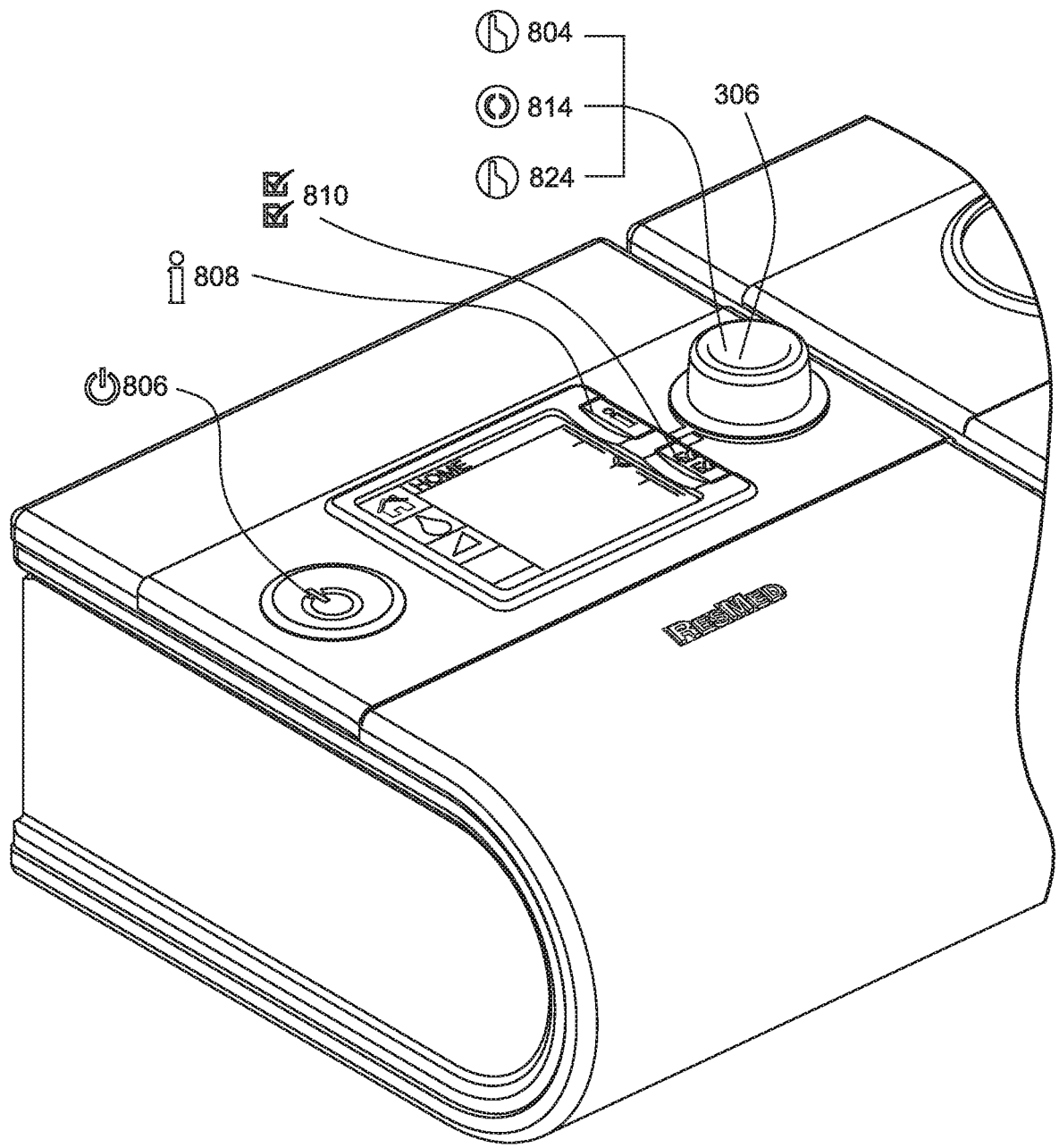
FIG. 9 shows a sample user interface and controls for a device.
Figure 10:
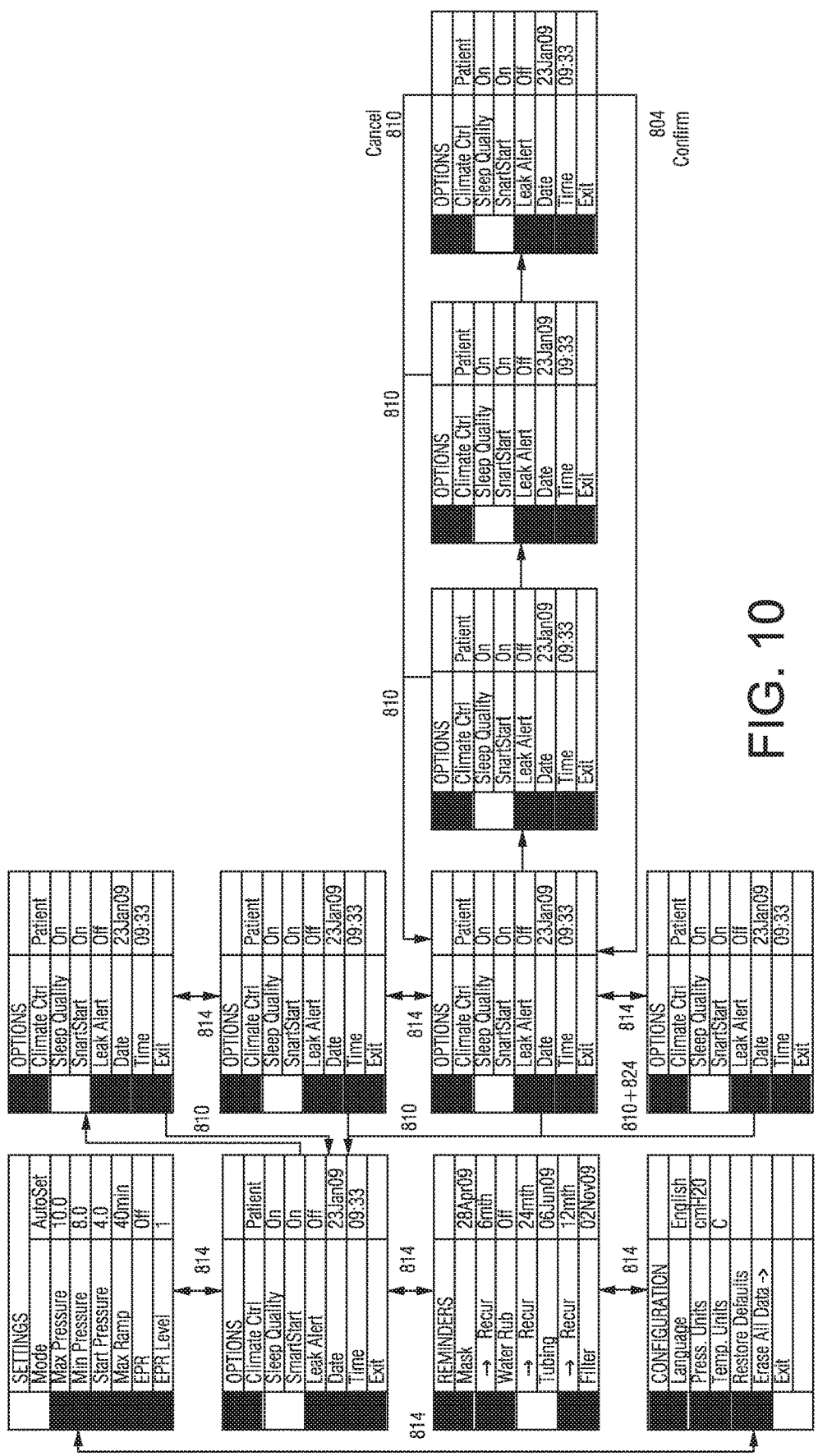
FIG. 10 is a flowchart of a sample menu structure for the device control of FIG. 8, with the controls used to navigate the menu.

FIGS. 8 to 10 illustrate a control dial and user interface arrangement according to one embodiment of the invention.

FIG. 8 shows a table of symbols which are used in discussion of the operation of the control interface further exemplified in FIGS. 9 and 10. The symbols identify the action required to perform a function within the user interface. Symbol 806 refers to the action of pushing the start/stop button 306. Symbols 810 and 808 refer to pushing the setup menu key 310 and info menu key 308 respectively. Symbol 802 indicates a waiting time for an action to be processed. Symbols 804, 814 and 824 relate to actions performed using the rotary dial 304. The actions performed are pushing the dial 804, turning or rotating the dial 814 and pushing and holding the dial pressed for a period of time, such as 3 seconds 824.

FIG. 9 illustrates a sample user interface for a medical device, such as a CPAP respiratory apparatus or a humidifier therefor, along with the user functions associated with each. The interface includes a graphical interface such an LCD or other suitable screen for displaying a control menu, with controls nearby on the device for the user to control operation of the device by selection of menu items.

In the example of FIG. 9, the controls include a start/stop button 304, an information ("info") button 308 and setup button 310 adjacent the screen 302, and a rotary control dial 306. In the illustrated user interface arrangement, the start/stop, information and setup buttons may be simply push buttons, optionally backlit to aid user operation in the dark. The dial may be of the type adapted for continuous rotation, or for shuttling left or right of a central position within a limited range of rotation, and is also adapted to operate as a push button to allow additional user input in that manner.

As can be seen in FIGS. 8 to 10, there are three different operations of the rotary dial 306 by which the user may input information: by (1) pushing the dial; (2) turning the dial; and (3) pushing and turning the dial for a set period, for example for 3 seconds.

As described later with reference to FIG. 10, combinations of controls may also be used.

FIG. 10 shows a schematic sample of a control menu structure and the control operations used to navigate within and between the menus and to select items.

As shown in FIG. 10, a top level menu is shown as shown at the left side of FIG. 8, with menu items SETTINGS, OPTIONS, REMINDERS and CONFIGURATION. These menu items are represented graphically along the left hand side of the screen display, with the currently selected menu item highlighted as denoted by the lighter square along the left side of each screen display in FIG. 10, and the corresponding text shown at the top of the screen display.

By way of example, FIG. 10 further shows expansion of the OPTIONS and DATE menu items.

To navigate up or down within a menu, the user turns the rotary control dial left or right, and to access or select the highlighted menu item the user presses the control dial. Navigation back up one menu level may be for example by pressing the setup button 306, or by pressing both the control dial 306 and the setup button 310, as shown in FIG. 10.

In accordance with an embodiment of the invention, the user controls incorporate an intuitive control which compensates for user preferences in the direction in which that user rotates the control dial to navigate the menu. In particular, the menu format is arranged so that entry into a menu level is at a known position in the menu list, preferably at one end of the menu for example at the top menu item SETTINGS in the top level menu shown in FIG. 10, or at the item Climate Cntrl within the OPTIONS menu while the EXIT from that menu level is at the opposite end of that menu list.

The direction that the user initially rotates the control dial 306 to navigate away from that first menu item is detected and that rotary direction is assigned to be the down direction within the menu, so that further rotation of the dial in that direction continues downward navigation within the menu, while rotation in the opposite direction causes upwards navigation through the menu. Therefore, in the example of FIG. 10, if the user initially turns the dial anticlockwise to navigate away from the SETTINGS menu item in the top menu level to the SLEEP QUALITY menu item, then turning the dial anticlockwise is assigned to be the down direction to navigate down the menu items list and turning clockwise to be the up direction to navigate back up the menu items list.

In this way, the device controls will adjust automatically to the user preference on the dial operation.

The assignment of the up and down directions may be re-assigned each time a new menu level is entered, or may be retained for a longer duration, for example for the duration of the user session.

The intuitive dial control may be incorporated by any suitable means, for example within the computer control software of the device.

It will be appreciated also that the intuitive dial control in accordance with the exemplary embodiment may have application beyond the medical respiratory devices to which the invention relates primarily, to other devices which employ a rotary control dial.

7 Other Features

The flow generator preferably incorporates automatic switching between modes of the device, as described below:

Preferably in Patient Run Mode—When there is no interaction with the UI for a waiting period of 30 seconds, the UI will automatically return to either, the Patient Climate Control, Humidifier Level, Heated Tube Level or Home Screen depending what is attached. This allows the patient to adjust their humidity or heated tube setting during the night without looking at the display.

In one form "no interaction" can include minor interaction. For example, the user interface may return to a Patient Climate Control mode in spite of a short period of interaction that may result from bumping or touching the user interface.

Whilst a period of 30 seconds is preferred for the required period, in other forms, other waiting periods may be used, such as about 5 seconds, or several minutes.

Preferably in Standby Mode—When there is no interaction with the UI for the Idle timeout duration, the UI will automatically exit the Patient Setup Menu and go to the Patient Home Screen in the Idle state.

Preferably during Run Mode in the Patient Menu, the UI will not allow the user to enter the Patient Info Menu.

In one form, when adjusting a numeric parameter, when the dial is tamed slowly, it will adjust a parameter in minimal increments, eg 0.2 cmH2O per encoder increment, but when the dial is turned quickly, it will adjust the parameter in whole number increments; eg 1.0 cm H2O per encoder increment.

In a preferred form, the controls of the user interface are located on the flow generator. Hence some controls perform dual function of being able to control the humidifier as well as aspects of the flow generator. For example the dial may be able to control ramp time, pressure and humidification (including climate control level, heated tube temperature and humidity).

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise, comprised and comprises where they appear.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein. It will further be understood that any reference herein to known prior art does not, unless the contrary indication appears, constitute an admission that such prior art is commonly known by those skilled in the art to which the invention relates.

The invention claimed is:

1. An apparatus for treating sleep disordered breathing (SDB) in a patient, the apparatus comprising:
   a flow generator configured to deliver a supply of air at positive pressure in the range of 4 to 25 cmH2O;
   a display configured to display a plurality of screens to a user;
   a set of controls operable by the user; and
   a controller configured to control operation of the flow generator and the display, receive user input from the set of controls, detect whether at least one accessory device is connected to the apparatus, and determine the identity of the at least one accessory device, if the controller detects at least one accessory device connected to the apparatus;
   wherein the controller is configured to instruct the display to display a first screen of the plurality of screens based on whether the controller detects at least one accessory device connected to the apparatus and the identity of the at least one accessory device determined by the controller, if the controller detects at least one accessory device connected to the apparatus;
   wherein when the display is displaying the first screen and the controller receives user input from the set of controls, the controller is configured to instruct the display to display a second screen of the plurality of screens in response to the user input; and
   wherein when the display is displaying the second screen and the controller determines that a predetermined period of time has elapsed after the controller received user input without receiving further user input, the controller is configured to instruct the display to display the first screen.

2. The apparatus of claim 1, wherein the at least one accessory device is a humidifier and/or a heated tube.

3. The apparatus of claim 1, wherein the flow generator is operable in a plurality of modes including a standby mode, a mask fitting mode, a run mode, and an error mode.

4. The apparatus of claim 3, wherein when the flow generator is in the standby mode or the run mode, the first screen and the second screen each is a different one of a patient climate control screen, a humidifier level screen, a heated tube level screen, and a home screen.

5. The apparatus of claim 3, wherein when the flow generator is in the standby mode, the first screen is a patient home screen and the second screen is a patient setup menu screen.

6. The apparatus of claim 3, wherein when the flow generator is in the standby mode, the flow generator is configured not to deliver the supply of air at positive pressure.

7. The apparatus of claim 3, wherein when the flow generator is in the mask fitting mode, the flow generator is configured to deliver the supply of air at positive pressure to allow the user to check for leaks between a mask and the patient's face and, if necessary, adjust the mask.

8. The apparatus of claim 3, wherein when the flow generator is in the run mode, the flow generator is configured to deliver the supply of air at positive pressure to treat sleep disordered breathing.

9. The apparatus of claim 3, wherein when the flow generator is in the error mode, the controller has detected an error and the flow generator is configured not to deliver the supply of air at positive pressure.

10. The apparatus of claim 1, wherein the predetermined period of time is thirty seconds.

11. The apparatus of claim 1, wherein the set of controls are located on the flow generator.

12. The apparatus of claim 1, wherein the set of controls includes a dial to control ramp time, pressure, humidification, climate control level, and/or heated tube temperature and humidity.

13. The apparatus of claim 1, wherein if the controller does not detect at least one accessory device connected to the apparatus, the first screen of the plurality of screens is a flow generator default screen that is configured to enable adjustment, using the set of controls, of a flow generator operational parameter that is associated with operation of the flow generator, and
   wherein if the controller detects at least one accessory device connected to the apparatus, the first screen is a screen that is configured to enable adjustment, using the set of controls, of an accessory device operational parameter that is associated with operation of the at least one accessory device.

14. The apparatus of claim 13, wherein the flow generator operational parameter is a set treatment pressure or a ramp time.

15. The apparatus of claim 13, wherein the at least one accessory device is a humidifier and the accessory device operational parameter is a humidity parameter of the humidifier.

16. The apparatus of claim 13, wherein the at least one accessory device is a heated tube and the accessory device operational parameter is a heated tube temperature parameter.

17. The apparatus according of claim 13, wherein the at least one accessory device is a humidifier and a heated tube and the accessory device operational parameter is a climate control parameter.

18. The apparatus of claim 13, wherein the set of controls further comprises a first control and a second control, and
   wherein, when the display is displaying the first screen, the flow generator operational parameter or the accessory device operational parameter is adjustable in response to user interaction with the first control, and the display is configured to display the second screen in response to user interaction with the second control.

19. The apparatus of claim 13, further comprising a backlight configured to indicate different states of the flow generator.

\* \* \* \* \*